Figure 1:
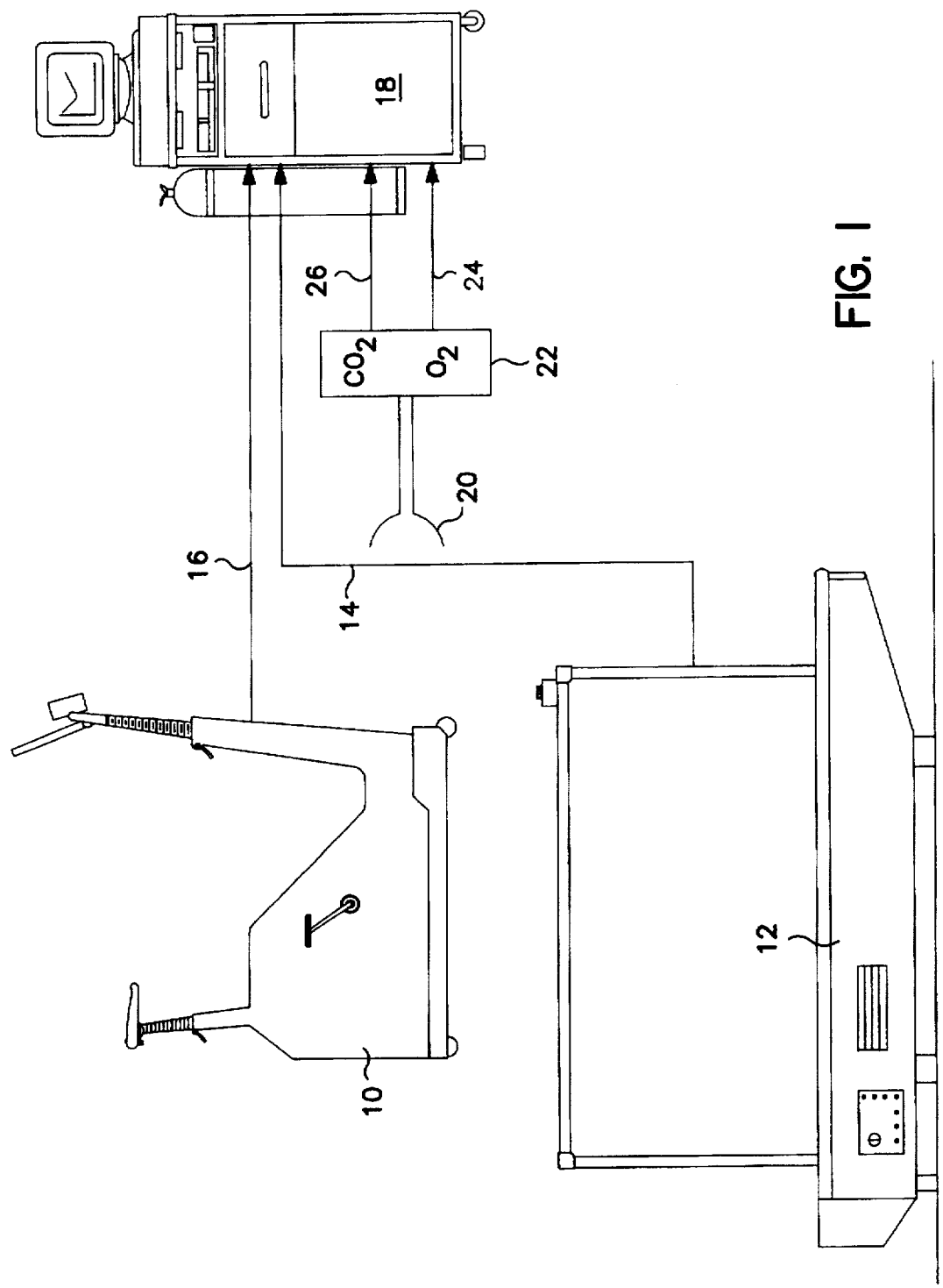

United States Patent [19]

Stegmann

[11] Patent Number: 5,782,772
[45] Date of Patent: Jul. 21, 1998

[54] DEVICE AND METHOD FOR DETERMINATION OF THE INDIVIDUAL ANAEROBIC THRESHOLD OF A LIVING ORGANISM

[76] Inventor: Heiner Stegmann, Friedrich-Ebert Anlage 25, D-63411 Hanau, Germany

[21] Appl. No.: 696,975
[22] PCT Filed: Feb. 27, 1995
[86] PCT No.: PCT/EP95/00711
  § 371 Date: Dec. 20, 1996
  § 102(e) Date: Dec. 20, 1996
[87] PCT Pub. No.: WO95/22929
  PCT Pub. Date: Aug. 31, 1995

[30] Foreign Application Priority Data

Feb. 26, 1994 [DE] Germany ............. 44 06 286.9

[51] Int. Cl.$^6$ ............................................. A61B 5/08
[52] U.S. Cl. ............... 600/520; 600/528; 600/529; 600/483; 600/484; 600/531; 600/513
[58] Field of Search ............... 128/670, 671, 128/668, 716, 719, 718, 700, 704, 707, 725; 600/483, 484, 481, 529, 532, 531, 513, 517, 520, 533

[56] References Cited

U.S. PATENT DOCUMENTS

| | | | |
|---|---|---|---|
| 4,930,519 | 6/1990 | Anderson et al. | 128/719 |
| 4,981,136 | 1/1991 | Chance | 128/707 |
| 5,297,558 | 3/1994 | Acorn et al. | 128/719 |
| 5,410,472 | 4/1995 | Anderson | 128/707 |
| 5,448,998 | 9/1995 | Ito et al. | 128/707 |
| 5,598,849 | 2/1997 | Browne | 128/707 |

*Primary Examiner*—Lee S. Cohen
*Assistant Examiner*—Stephen Huang
*Attorney, Agent, or Firm*—Bierman, Muserlian and Lucas

[57] ABSTRACT

A device for dynamic recording of respiratory, metabolic and/or ventilatory quantities during a process or influence conducive to lactate production, having a data processing facility (18) incorporating a display unit and also a computing unit, and having a device (20) connected via an analysis instrument (22) to said data processing facility for determination of respiratory minute volume and also of $O_2$ content of $CO_2$ content of said respiratory minute volume of inhaled or exhaled air, wherein with said computer unit using the respiratory measuring quantities of respiratory minute volume $V_e$ of the $O_2$ content of the respiratory minute volume $V_{o2}$ and of the $CO_2$ content of the respiratory minute volume $V_{co2}$ according to an algorithm, to permit determination of a quantity x as a function of the work performed per unit of time (P).

5 Claims, 2 Drawing Sheets

DEVICE AND METHOD FOR DETERMINATION OF THE INDIVIDUAL ANAEROBIC THRESHOLD OF A LIVING ORGANISM

FIELD OF THE INVENTION

The invention relates to a device for dynamic recording of the respiratory, metabolic and/or ventilatory quantities during, a process or influence conducive to lactate production, having a data processing facility incorporating a display unit and also a computing unit, and having a device such as a mask connected via an analysis instrument to the data processing facility for determination of the respiratory minute volume and also of the $O_2$ content and $CO_2$ content of the respiratory minute volume of the inhaled or exhaled air.

The invention further relates to a method for reproducible assessment of the physical capacity of a living organism such as a human being during a process or influence conducive to lactate production by determination of the "individual anaerobic threshold".

STATE OF THE ART

The "individual anaerobic threshold" (Lactate Kinetics and Individual Anaerobic Threshold, Stegmann et al. International Journal of Sports Medicine, S. 160–165, Georg. Thieme Verlag Stuttgart, 1981) is a fixed and clearly reproducible value. This "individual anaerobic threshold" is also of importance for physiological parameters such as assessment of the physical capacity, blood pressure under load and coronary heart disease.

According to the prior art, the "individual anaerobic threshold" is obtained by determining the lactate, i.e. the lactic acid in the blood. The change in the proportion of lactic acid in the blood is determined as a function of the work performed per unit of time.

The drawback of this method is that blood samples, preferably from the earlobe, must be taken continually from the person whose individual anaerobic threshold is to be determined. These measures are not only laborious, but also permit determination of the "individual anaerobic threshold" only after a time-lag.

It is furthermore known from the prior art that breathing equivalent $O_2$ $$\left( \frac{\dot{V}_e}{\dot{V}_{O_2}} \right)$$

and the breathing equivalent $CO_2$ $$\left( \frac{\dot{V}_e}{\dot{V}_{CO_2}} \right),$$

where the ventilation parameters are determined by a device of the above type, are plotted over time. Here the "anaerobic threshold" was defined as the point in which a steep rise of the breathing equivalent $O_2$ is registered without the curve for the breathing equivalent $CO_2$ rising. For determination of the "anaerobic threshold", however, it is still necessary to ascertain the lactate in the blood of the person under strain (H. A. Davis and G. C. Gass: The anaerobic threshold as determined before and during lactic acidosis, European Journal of Applied Physiology, Springer-Verlag 1981).

It is furthermore proposed that a fixed blood lactate concentration be given (J. A. Davis u.a.: Does the gas exchange anaerobic threshold occur at a fixed blood lactate concentration of 2 or 4 m/M?, International Journal Sports Medicine 4 (1983), S. 89– 93, Georg Thieme Verlag Stuttgart). In this case the breathing equivalent $O_2$ $$\left( \frac{\dot{V}_e}{\dot{V}_{O_2}} \right)$$

and the breathing equivalent $CO_2$ $$\left( \frac{\dot{V}_e}{\dot{V}_{CO_2}} \right)$$

are again measured and a systematic rise of the breathing equivalent $O_2$ is defined as the "anaerobic threshold" when the breathing equivalent $CO_2$ does not undergo any marked rise at this point. This evaluation does however involve major inaccuracies and does not permit the determination of the "individual anaerobic threshold".

The problem underlying the present invention is to permit the determination of the individual anaerobic threshold of a human being without having to continually determine the lactate by taking blood samples. It should be possible to determine the individual anaerobic threshold with high precision.

SUMMARY OF THE INVENTION

The problem is solved in accordance with the invention in that the previously described device is used for determination of the individual anaerobic threshold, where the computer unit uses the respiratory measuring quantities of respiratory minute volume $V_{e2}$ of the $O_2$ content of respiratory volume $V_{O2}$ and of the $CO_2$ content of respiratory volume $V_{CO2}$ according to an algorithm $$x = \frac{\dot{V}_e}{\sqrt[3]{(\dot{V}_{CO_2}^2 \dot{V}_{O_2})}}$$

to permit determination of a quantity x as a function of the work performed per unit of time (P), in that a curve is adapted to the values x=f(P) or a curve is passed through these values, with a load value PIAT corresponding to the individual anaerobic threshold determining a point of the curve x=f(P) at which the derivation dx(P)/dP is zero or has a maximum discontinuity.

In accordance with the invention, it has surprisingly become clear that solely the respiratory minute volume and the $CO_2$ or $O_2$ contents thereof must be ascertained to determine the individual anaerobic threshold directly from these values, without the need for a continual lactate determination as a result.

The idea underlying the present invention is that the $CO_2$ saturation SAT ($CO_2$) is proportional to the square of the partial pressure of $CO_2$ p ($CO_2$) and the $O_2$ saturation SAT ($O_2$) is linear to the partial pressure $O_2$ p ($O_2$). Use is also made of the fact that the proportions are subjected to considerable change by the formation of lactate.

In accordance with the invention, the ascertained respiratory minute volumes and their $O_2$ and $CO_2$ contents are correlated, in order to obtain on the basis of the equation $$x = \frac{\dot{V}_e}{\sqrt[3]{(\dot{V}_{CO_2})\dot{V}_{O_2}}}$$

a value x (as the breathing equivalent for gas pressure) which—at its minimum or final rise, or mathematically speaking at a point at which the time derivation dx(t)/dt is zero or has a maximum discontinuity—gives or defines a load value PIAT (Point of Individual Anaerobic Threshold) corresponding to the individual anaerobic threshold.

The determination of the change in parameters can take place here as a function of a gradual increase in the activity of test person. It is of course also possible that a continuous increase in performance is observed.

It is however possible for every further operation causing a lactate accumulation in the blood to be used for determination of the individual anaerobic threshold, i.e. the threshold performance. As examples of this, oxygen removal, intoxication by medicines, reduction of the heart output or lactate infusion may be mentioned.

Generally, therefore, a method is proposed in accordance with the invention for reproducible assessment of the physical capacity of a living organism such as a human being during a process or influence conducive to lactate production by the determination of the individual anaerobic threshold, wherein the respiratory minute volume ($V_e$) as well as the $O_2$ and $CO_2$ contents of the respiratory minute volume ($V_{O2}$; $V_{CO2}$) are measured characterized in that as a function of the process or influence conductive to lactate production from the measured values of respiratory minute volume $\dot{V}_e$ and of the $O_2$ and $CO_2$ contents of the respiratory minute volume ($\dot{V}_{O_2}$; $\dot{V}_{CO_2}$) quantity x is determined on the basis of the algorithm from $$x = \frac{\dot{V}_e}{\sqrt[3]{(\dot{V}_{CO_2})\dot{V}_{O_2}}}$$

as a function of the time in which the influence or process conducive to lactate production acts on the living organism, and that a curve is adapted to or passes through the values x=f(t), with a value (PIAT) corresponding to the individual anaerobic threshold being determined by a point on the curve at which the time derivation dx(t)/d(t) is zero or has a maximum discontinuity.

Further details, advantages and features of the invention are shown not only in the claims and in the features therein, singly and/or in combination, but also in the following description of a design examples shown in the drawing.

Figure 2:
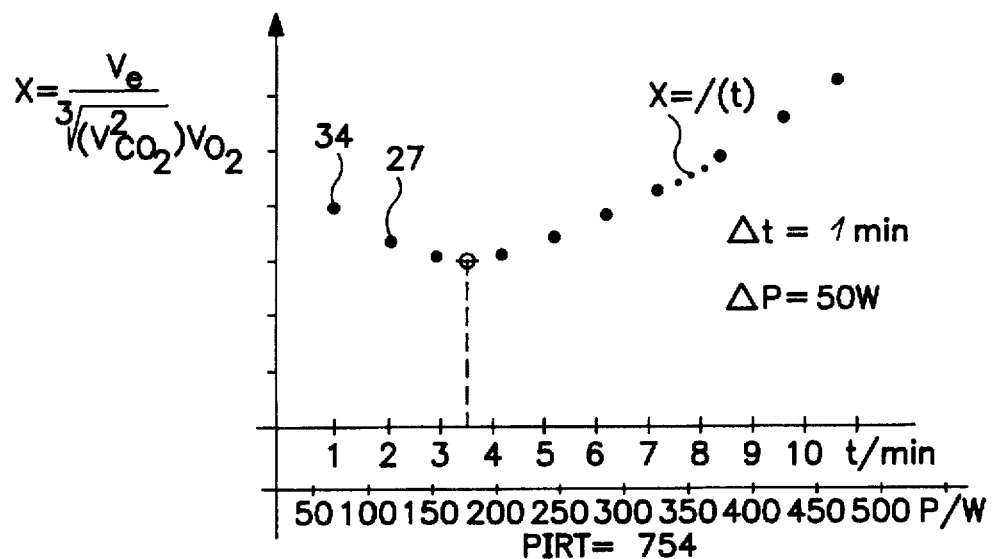
Figure 3:
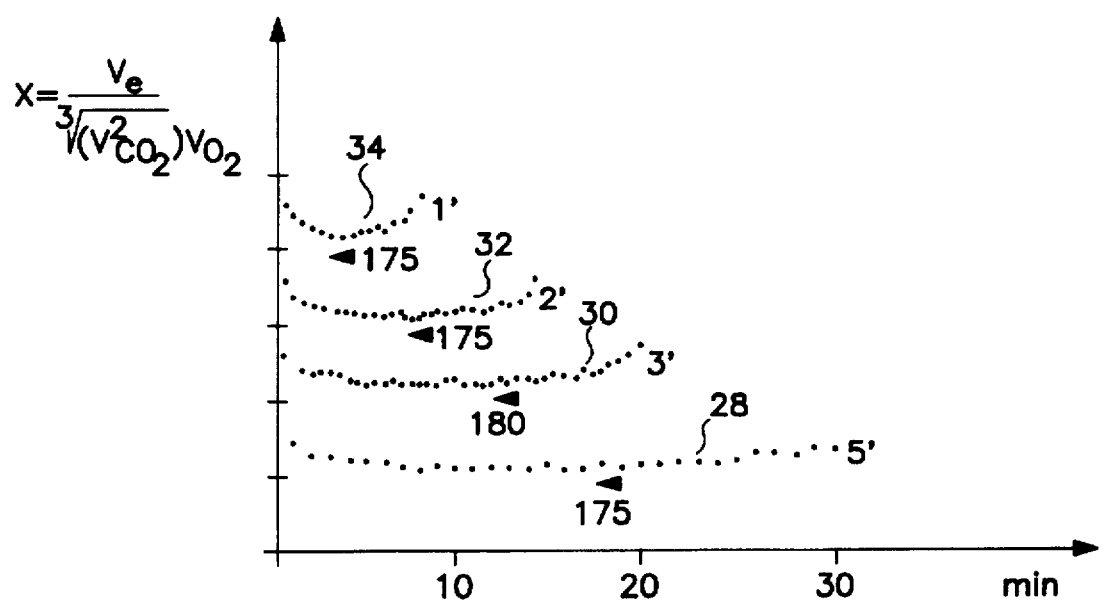

In the drawing:

FIG. 1 shows a test array for determination of the individual anaerobic threshold, FIG. 2 shows a graph for determination of the individual anaerobic threshold and FIG. 3 shows a plurality of graphs for determination of the individual anaerobic thresholds under differing types of load.

To ascertain the individual anaerobic threshold of a test person, the latter must perform work over a period of time. Parallel to this, the respiratory minute volume $\dot{V}e$ and the $CO_2$ and $O_2$ contents of the test person are determined.

To perform the load measurement, a bicycle ergometer (10) or alternatively for example a treadmill (12) can be used. The appropriate devices (10) or (12) are connected via cables (14) and (16) to a data processing facility (18) in order to ascertain the work performed per unit of time.

To ascertain the respiratory minute volume and/or its $CO_2$ and $O_2$ contents, the test person is fitted with a mask (20) or mouthpiece shown purely schematically in FIG. 1.

The air inhaled by the test person and the $O_2$ and $CO_2$ contents present in the exhaled air are determined using an analysis instrument (22) in order to then pass the values to the data processing facility (18) via cables (24) and (26).

Using the thus measured/ascertained values, i.e. the work performed per unit of time, the respiratory minute volume $\dot{V}e$ and the $CO_2$ and $O_2$ consumption of the latter, the value x is then determined on the basis of $$x = \frac{\dot{V}_e}{\sqrt[3]{(\dot{V}_{CO_2})\dot{V}_{O_2}}}$$

and plotted over time or performance to obtain the measuring points shown in FIGS. 2 and 3.

A measuring process can be explained on the basis of the graph x=f(t). After a unit of time $\Delta t$ (in this case $\Delta t$=1 min.) and a gradually increased performance $\Delta p$ (in this case $\Delta p$=50 W), measuring values x over the time t are plotted per unit of time. After completing the measurement, the measuring points are described by a function x=f(t), that can be ascertained with the aid of a computer. In other words, the measuring curves are determined by the value x=f(t) being ascertained using the previously mentioned equation for every unit of time in which the load is increased by a constant value.

The curve x=f(t) is evaluated by forming the time derivation. The point in the curve in which the time derivation is 0 or has a maximum discontinuity corresponds to a load value PIAT corresponding to the individual anaerobic threshold.

FIG. 3 shows various measuring curves (28), (30), (32), (34) differing in that the time interval of the load change $\Delta t$ increases from a unit of time $\Delta t$=1 min. (curve 34) up to a unit of time $\Delta t$=5 min. (curve 28). The performance $\Delta p$ increased per unit of time corresponds in all measuring curves to a value of $\Delta p$=50 W.

With loading in a time interval of $\Delta t \geq 1$ min. until—for example—$\Delta t$=5 min., it can be seen that for the test person for whom the curves (28), (30), (32) and (34) were ascertained, an individual anaerobic threshold of PIAT 175±5 W can be determined. This corresponds to the point at which anaerobic work is performed when capacity is expended.

I claim:

1. A device for dynamic recording of respiratory, metabolic and/or ventilatory quantities during a process or influence conducive to lactate production, comprising:

a data processing unit and also a computing unit, a second device (20) connected via an analysis instrument (22) to said data processing unit for determination of respiratory minute volume and also of O2 content or CO2 content of said respiratory minute volume of inhaled or exhaled air, wherein said computing unit using the respiratory measuring quantities of respiratory minute volume Ve of the O2 content of respiratory minute volume VO2 and of the CO2 content of the respiratory minute volume VCO2 according to an algorithm, to permit determination of a quantity x as a function of work performed per unit of time (P), said device for dynamic recording is used for determination of individual anaerobic threshold, with said computing unit using the respiratory measuring quantities of respiratory minute volume Vel of the O2 content of respiratory minute volume VO2 and of the CO2 content of respiratory minute volume VCO2 according to an algorithm $$x = \frac{\dot{V}_e}{\sqrt[3]{(\dot{V}_{CO_2}^2)\dot{V}_{O_2}}}$$

to permit determination of a quantity x as a function of the work performed per unit time (P), wherein
a curve is adapted to values of x represented by x=f(P) or a curve is passed through these values, with a load value (PIAT)
corresponding to said individual anaerobic threshold determining a point of the curve x=f(P) at which a derivative dx(P)/dP is zero or has a maximum discontinuity.

2. A device according to claim 1, comprising
a means to gradually set a change in the work performed.

3. A device according to claim 1, comprising
a means to continuously set a change in the work performed.

4. A method for reproducible assessment of physical activity of a living organism during a process or influence conducive to lactate production by determination of the individual anaerobic threshold, wherein the method comprises the steps of, measuring the respiratory minute volume (Ve) as well as the O2 and CO2 contents of respiratory minute volume (VO2; VCO2), determining a quantity x, as a function of said process or influence conducive to lactate production from the measured values of the respiratory minute volume Ve and of O2 and CO2 contents of said respiratory minute volume (VO2; VCO2), based of an algorithm $$x = \frac{\dot{V}_e}{\sqrt[3]{(\dot{V}_{CO_2}^2)\dot{V}_{O_2}}}$$

as a function of time in which said influence or process conducive to lactate production acts on the living organism, and wherein a curve is adapted to or passes through values x=f(t), with a value (PIAT) corresponding to said individual anaerobic threshold being determined by a point on the curve at which time derivation dx(t)/d(t) is zero or has a maximum discontinuity.

5. A method according to claim 4, wherein
said influence or process conducive to lactate production is caused by work performed by the living organism per unit of time, by lactate infusion, by intoxication by medicines and/or reduction of the heart output.

* * * * *